(12) United States Patent
Ellis et al.

(10) Patent No.: US 6,395,008 B1
(45) Date of Patent: May 28, 2002

(54) STENT DELIVERY DEVICE USING STENT CUPS AND MOUNTING COLLARS

(75) Inventors: Louis G. Ellis, St. Anthony; Andrew J. Dusbabek, Dayton, both of MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 08/701,979

(22) Filed: Aug. 23, 1996

(51) Int. Cl.⁷ ................................................. A61F 11/00
(52) U.S. Cl. ........................................ 606/108; 606/195
(58) Field of Search .................................. 606/108, 194, 606/195, 198

(56) References Cited

U.S. PATENT DOCUMENTS

| | | |
|---|---|---|
| 4,328,056 A | 5/1982 | Snooks |
| 4,338,942 A | 7/1982 | Fogarty |
| 4,423,725 A | 1/1984 | Baran et al. |
| 4,608,984 A | 9/1986 | Fogarty |
| 4,733,665 A | 3/1988 | Palmaz |
| 4,740,207 A | 4/1988 | Kreamer |
| 4,744,366 A | 5/1988 | Jang |
| 4,848,343 A | 7/1989 | Wallstein et al. |
| 4,875,480 A | 10/1989 | Imbert |
| 4,950,227 A | 8/1990 | Savin et al. |
| 5,007,926 A | 4/1991 | Derbyshire |
| 5,026,377 A | 6/1991 | Burton et al. |
| 5,037,392 A | 8/1991 | Hillstead |
| 5,049,132 A | 9/1991 | Shaffer et al. |
| 5,108,416 A * | 4/1992 | Ryan et al. .................. 606/194 |
| 5,116,318 A | 5/1992 | Hillstead |
| 5,158,548 A | 10/1992 | Lau et al. |
| 5,192,295 A * | 3/1993 | Danforth et al. ............ 606/194 |
| 5,226,880 A | 7/1993 | Martin |
| 5,226,889 A | 7/1993 | Sheiban |
| 5,242,399 A | 9/1993 | Lau et al. |
| 5,290,306 A | 3/1994 | Trotta et al. |

(List continued on next page.)

FOREIGN PATENT DOCUMENTS

| | | | |
|---|---|---|---|
| EP | 0 266 957 A2 | 5/1988 | |
| EP | 0 442 657 A2 | 8/1991 | |
| EP | 0 553 960 A1 | 8/1993 | |
| EP | 0 274 846 B1 | 2/1994 | .......... A61M/29/02 |
| EP | O 707 837 A1 | 4/1996 | |
| WO | WO96/03072 A1 | 2/1996 | |
| WO | WO96/03092 A1 | 2/1996 | |

OTHER PUBLICATIONS

Julio C. Palmaz et al., 156 Radiology 73 (1985), Expandable Intraluminal Graft: a Preliminary Study.

*Primary Examiner*—Justine R. Yu
(74) *Attorney, Agent, or Firm*—Vidas, Arrett & Steinkraus PA

(57) ABSTRACT

An assembly and a method to deliver and deploy and inflation expandable stent is described. The assembly has a catheter with an annular collar is coaxially located on the catheter distal end. An expandable balloon, in a contracted state, is coaxially mounted over the collar at the catheter distal end. A stent, in a reduced configuration, is coaxially mounted on the balloon and conformed to the catheter and collar. At least one cup is coaxially mounted on the catheter distal end. The cup and collar are cooperate to retain the end portion of the reduced stent on the catheter. The balloon is inflated to expand the stent and release the stent from the cup or cups. The cup can be axially spaced from the collar. The cup can be fixed to the catheter or can be freely sliding on the catheter. The cup can overlie at least a portion of the collar. The collar can be shaped as a single member with the catheter.

35 Claims, 2 Drawing Sheets

U.S. PATENT DOCUMENTS

| | | |
|---|---|---|
| 5,342,305 A | 8/1994 | Shonk |
| 5,344,402 A | 9/1994 | Crocker |
| 5,358,487 A | 10/1994 | Miller |
| 5,378,237 A | 1/1995 | Boussignac et al. |
| 5,403,341 A | 4/1995 | Solar |
| 5,405,380 A | 4/1995 | Gianotti et al. |
| 5,409,495 A | 4/1995 | Osborn |
| 5,415,664 A | 5/1995 | Pinchuk |
| 5,445,646 A * | 8/1995 | Euteneuer et al. .......... 606/198 |
| 5,447,497 A | 9/1995 | Sogard et al. |
| 5,453,090 A | 9/1995 | Martinez et al. |
| 5,458,615 A | 10/1995 | Klemm et al. |
| 5,470,313 A | 11/1995 | Crocker et al. |
| 5,507,768 A | 4/1996 | Lau et al. |
| 5,512,051 A | 4/1996 | Wang et al. |
| 5,534,007 A | 7/1996 | St. Germain et al. |
| 5,536,252 A | 7/1996 | Imran et al. |
| 5,545,209 A * | 8/1996 | Roberts et al. .............. 606/108 |
| 5,591,222 A * | 1/1997 | Susawa et al. .............. 606/195 |
| 5,632,760 A | 5/1997 | Sheiban et al. .............. 606/191 |

* cited by examiner

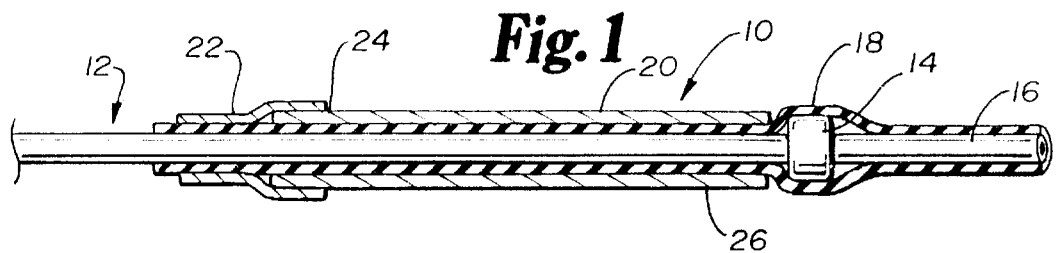
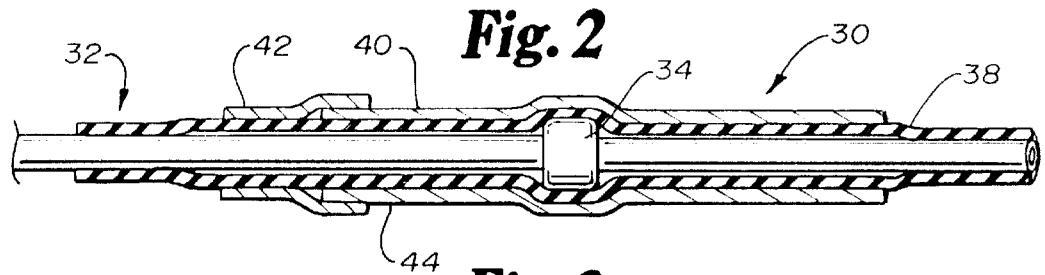
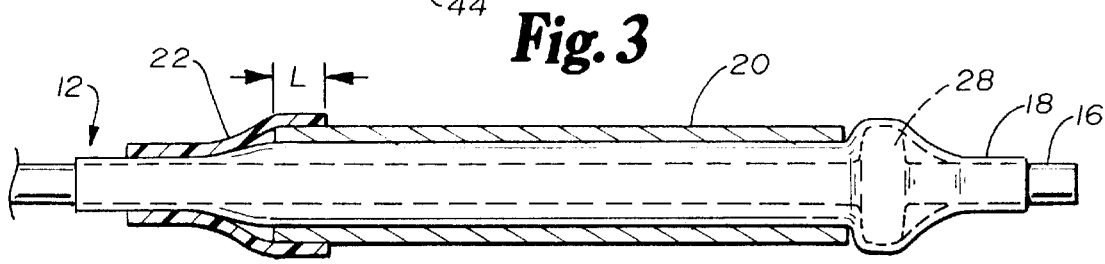
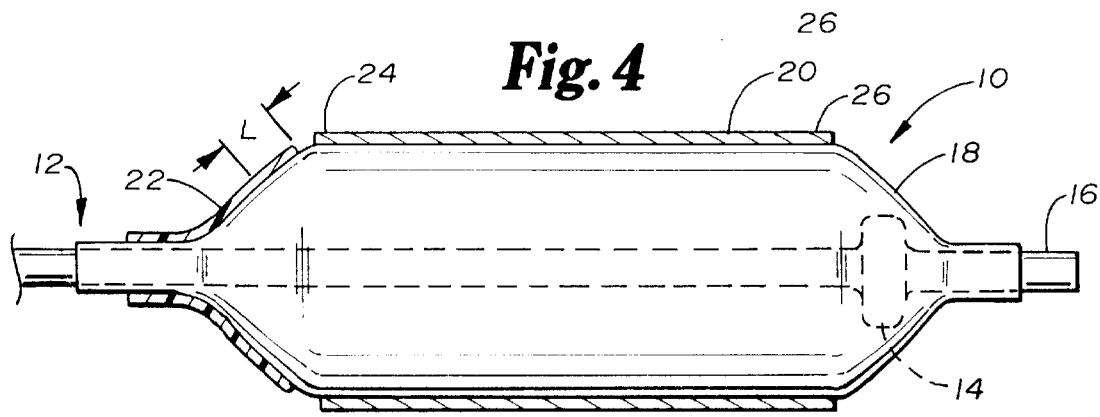
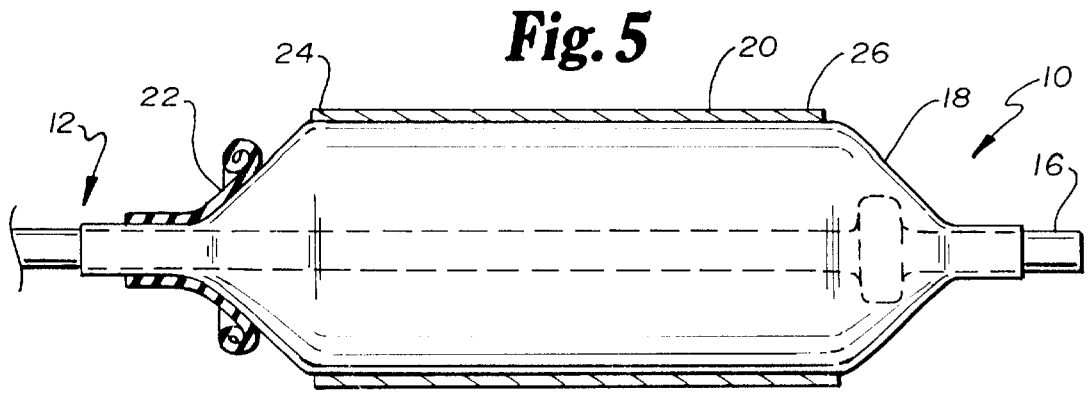

US 6,395,008 B1

STENT DELIVERY DEVICE USING STENT CUPS AND MOUNTING COLLARS

BACKGROUND OF THE INVENTION

1. Field of the Invention

This invention relates to an assembly and method for delivering and deploying an inflation expandable stent, particularly within a lumen of a body vessel. More specifically, this invention relates to the provision of a collar, ring or the like positioned beneath a stent expanding balloon, to be used in conjunction with a cup, positioned at an end portion of the stent, to maintain the stent on the catheter assembly during delivery to a stent deployment site.

2. Description of Relevant Art

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Inflation expandable stents are crimped to their reduced diameter about the delivery catheter, then maneuvered to the deployment site and expanded to the vessel diameter by fluid inflation of a balloon positioned between the stent and the delivery catheter. The present invention is particularly concerned with delivery and deployment of inflation expandable stents, although it is generally applicable to self-expanding stents when used with balloon catheters.

A preferred example is the stent described in PCT Application No. 960 3092 A1, published Feb. 8, 1996, the content of which is incorporated herein by reference.

In advancing an inflation expandable stent through a body vessel to the deployment site, there are a number of important considerations. The stent must be able to securely maintain its axial position on the delivery catheter, without translocating proximally or distally, and especially without becoming separated from the catheter. The stent, particularly its distal and proximal ends, must be protected to prevent distortion of the stent and to prevent abrasion and/or reduce trauma of the vessel walls.

Inflation expandable stent delivery and deployment assemblies are known which utilize restraining means that overlie the stent during delivery. U.S. Pat. No. 4,950,227 to Savin et al., relates to an inflation expandable stent delivery system in which a sleeve overlaps the distal or proximal margin (or both) of the stent during delivery. During inflation of the stent at the deployment site, the stent margins are freed of the protective sleeve(s). U.S. Pat. No. 5,403,341 to Solar, relates to a stent delivery and deployment assembly which uses retaining sheaths positioned about opposite ends of the compressed stent. The retaining sheaths of Solar are adapted to tear under pressure as the stent is radially expanded, thus releasing the stent from engagement with the sheaths. U.S. Pat. No. 5,108,416 to Ryan et al., describes a stent introducer system which uses one or two flexible end caps and an annular socket surrounding the balloon to position the stent during introduction to the deployment site. The content of all of these patents is incorporated herein by reference.

A number of inflation expandable stent delivery and deployment assemblies include features interior or exterior to the balloon to aid in positioning the stent during delivery. As described in European Patent Application No. EPO 707 837 A1 to Sheiban, the catheter is provided with concentric rings beneath the balloon. The compressed stent is coaxially mounted on the balloon in the Sheiban assembly, so that the entire length of the stent is between the bulges in the balloon caused by the underlying concentric rings. According to U.S. Pat. No. 4,733,665 (issued with re-examination certificate Jan. 11, 1994), to Palmaz, retainer ring members are disposed on the catheter adjacent (i.e., exterior and external) to the ends of the balloon and adjacent each end of the stent, to retain the stent in its contracted position on the assembly. The retainer ring members can be formed integral with the catheter.

Other patents of interest include U.S. Pat. No. 5,026,377 to Burton et al.; U.S. Pat. No. 5,158,548 to Lau et al.; U.S. Pat. No. 5,242,399 to Lau et al.; U.S. Pat. No. 5,415,664 to Pinchuk, and U.S. Pat. No. 5,453,090 to Martinez et al., all of which are incorporated herein by reference.

According to the present invention, it has now unexpectedly been discovered that, by providing one or two cups to contain one or both ends of the stent, in conjunction with the use of at least one annular collar, axially mounted on the catheter and underneath the balloon, securement of the stent is positively increased, particularly as the cup and collar are placed relatively close to each other. The collar can take any form and may be positioned immediately adjacent the end of the stent, such as opposite to the end of the stent contained by the cup or in a closer position relative to the cup. For example, the collar can also take the form of a mounting ring or cylinder positioned beneath the stent. Further, the collar can take the form of a sheath positioned under the length of the stent. The collar may be at least partially contained within one or both cups so that the stent, along with the intervening balloon, is effectively wedged between the cup and the collar.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

SUMMARY OF THE INVENTION

The present invention comprises an assembly for delivery and deployment of an inflation expandable stent. The assembly comprises a catheter having proximal and distal ends. An annular collar or the like is coaxially located on the catheter distal end. A fluid expandable balloon is coaxially mounted over the collar at the catheter distal end. The balloon is expandable from a contracted to an expanded state. A stent is coaxially mounted on the balloon. The stent is inflation expandable from a reduced to an enlarged condition, the reduced condition conforming the stent to the balloon, collar and catheter in the preferred embodiment. The stent has at least an end portion overlying the balloon. At least one cup is coaxially mounted on the catheter distal end. The cup has a first end portion which may overlie the stent end portion. The cup and collar are cooperatively constructed and arranged to retain the stent end portion on the catheter in the stent reduced condition when the balloon is in the contracted state. The balloon and catheter are cooperatively constructed and arranged to cause expansion of the balloon from the contracted to the expanded state to cause enlargement of the stent, including the stent end portion, from the reduced to the enlarged condition, and thereby release the stent end portion from the cup end portion. The cup may be axially spaced from the collar but preferably they are relatively close together. The second end portion of the cup may be fixed to the catheter. The cup may overlie at least a portion of the collar. The collar can be shaped as a single member with the catheter, that is integral with it or the collar may be a separate body mounted axially and positioned on the catheter. The collar may be a mounting ring or cylinder axially positioned between stent end portions under the stent and balloon. The collar may be a sheath under the stent and balloon.

This invention comprises a method for delivering and deploying a stent using the assembly as just described. The method comprises the following steps. A catheter is provided having proximal and distal ends. At least one collar is coaxially mounted at the catheter distal end. A fluid expandable balloon is coaxially mounted over the collar on the catheter distal end. A stent is provided, which is inflation expandable from a reduced to an enlarged condition. The stent, in the reduced condition, is coaxially mounted on the balloon so that at least an end portion of the stent overlies the balloon. At least one cup is provided which has first and second end portions. The cup is in an expanded form, and also has a retracted form. The expanded cup is coaxially mounted on the catheter distal end so that the cup first end portion restrains the stent end portion. The cup first end portion may restrain the stent end portion by overlying the stent end portion. The cup is contracted about the catheter and the stent end portion to fix the stent to the catheter. The cup and collar cooperate to retain the stent in the reduced condition. The assembly is delivered to a deployment site. The balloon is inflated to expand the stent to its enlarged condition, whereby the stent is released from the cup.

BRIEF DESCRIPTION OF THE FIGURES

FIG. 1 is a longitudinal cross-section of a stent delivery and deployment assembly of this invention showing a catheter with a collar mounted at the catheter distal end, an uninflated balloon mounted on the catheter over the collar, an unexpanded stent mounted on the balloon abutting the collar and a cup overlying the stent proximal end portion.

FIG. 2 is a longitudinal cross-section of another stent delivery and deployment assembly of this invention showing a catheter with a collar mounted as a mounting ring at the catheter distal end, an uninflated balloon mounted on the catheter over the mounting ring, an unexpanded stent mounted on the balloon overlying the mounting ring and a cup overlying the stent proximal end portion; note that the collar is positioned closer to the cup than in FIG. 1.

FIG. 3 is a longitudinal profile in partial cross-section of an assembly similar to that of FIG. 1, with a bulge formed under the uninflated balloon at the catheter distal end.

FIG. 4 is a longitudinal profile in partial cross-section of the assembly shown in FIG. 1 with the balloon inflated and the stent expanded, showing the cup end portion flared to release the stent.

FIG. 5 is a longitudinal profile, similar to FIG. 4, showing the cup end portion rolled proximally to release the stent.

DETAILED DESCRIPTION OF THE INVENTION

Figure 6:
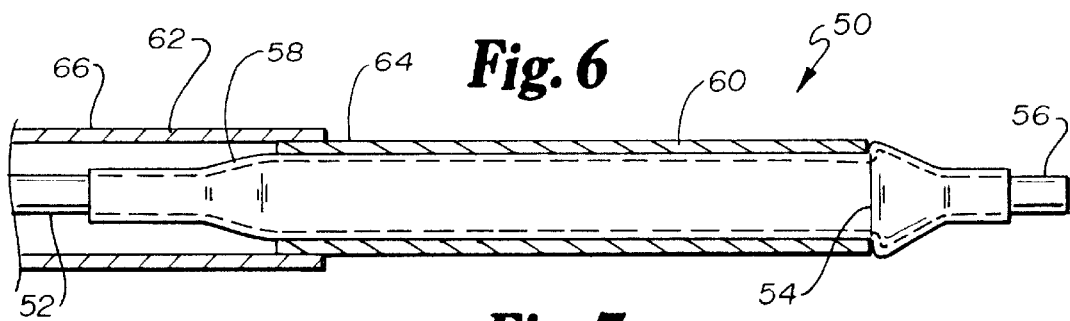
FIG. 6 is a longitudinal profile of yet another stent delivery and deployment assembly of this invention, with the balloon mounted on the catheter, which has a collar formed as a tapered single enlarged piece on the catheter, an unexpanded stent mounted on the unexpanded balloon abutting the collar and a cylindrical sleeve overlying the stent proximal end portion.

FIG. 1 shows a stent delivery and deployment assembly generally designated 10. A catheter 12 has a collar 14 coaxially mounted at the catheter distal end portion 16. An uninflated balloon 18 is coaxially mounted on catheter 12 over collar 14. An unexpanded stent 20 is coaxially mounted on the balloon 18 abutting but not overlying collar 14. A cup 22 coaxially overlies the stent proximal end portion 24. Cup 22 may be elastomeric or rigid, preferably elastomeric. Cup 22 is over-expanded over the stent 20, so that recoil of the cup 22 is sufficient to secure stent 20 in place and prevent it from being pulled off of the assembly 10 distally or proximally as assembly 10 is delivered to a deployment site in a body vessel. Cup 22 also protects the proximal end of stent 24 from inadvertently catching on anatomical structures or other things during maneuvering within the body or during loading and other handling. The ends of the stent may axially protrude and should be protected during maneuvering of stent 20 to keep stent 20 on assembly 10 in its contracted configuration and to maintain the structural integrity of stent 20. Collar 14 abuts the stent distal end 26 without underlying stent 20. The position of cup 22 overlying stent 20 and containing stent 20 against collar 14 increases the securement force maintaining stent 20 in its axial and radial position on catheter 12. FIG. 3 is similar to FIG. 1, showing a bulge 28 beneath the uninflated balloon 18 at catheter distal end 16.

Any of the various types of known stents may be used in the delivery system of this invention, even self-expanding stents which are partly balloon-expandable may be used, the balloon initiating release of the stent and/or finally seating the stent after self-expansion. However, ordinary balloon expandable stents are preferred and aforenoted.

FIG. 2 shows another stent delivery and deployment assembly generally designated 30. A catheter 32 has a collar coaxially mounted as a mounting ring 34 on the catheter. An uninflated balloon 38 is coaxially mounted on catheter 32 over mounting ring 34. An unexpanded stent 40 is coaxially mounted on balloon 38 overlying the mounting ring 34. A cup 42 overlies the stent proximal end portion 44 to secure the stent 40 in place and prevent it from being pulled off of assembly 30 distally or proximally, as assembly 30 is delivered to a deployment site in a body vessel. Cup 42 also protects the proximal end of stent 40 from inadvertently catching on anatomical structures during maneuvering within the body. The position of cup 42 overlying stent 40 together with the closer positioning of mounting ring 34 as compared to FIG. 1 increases the securement force maintaining stent 40 in its axial and radial position on catheter 42. The closer the mounting ring 34 is positioned to cup 42 the more securely the stent is held in place and interlocked between this cup and ring. When used in conjunction with mounting ring 34, cup 42 will also prevent the stent proximal segment 44 from opening up, i.e., increasing its diameter, and will keep the stent 40 locked onto the mounting ring 34. This will prevent stent 40 from moving on the catheter distally as well as proximally. This cup does not have to be an elastomer, but may be sufficiently rigid to prevent the stent 40 from expanding.

Cups 22, 42 of FIGS. 1–3 release stents 20, 40 when balloons 18, 38 are inflated during deployment. Cups 22, 42 can, for example, flare radially outward as illustrated with reference to FIG. 4, roll axially away from stents 20, 40 as illustrated with reference to FIG. 5, or slide axially away from stents 20,40 as illustrated with reference to FIGS. 6 and 7. Also, the cups may be formed with axial areas of weakness which split on balloon inflation, as described in the aforenoted Savin patent.

FIG. 4 shows an assembly generally designated 10 as shown in FIGS. 1 and 3 with balloon 18 inflated and stent 20 expanded, showing the cup 22 end portion flared to release stent 20. As noted above, cup 22 may be elastomeric or rigid. The dimension L is short enough and the material of cup 22 is sufficiently elastic so that cup 22 flares out and is no longer in contact with stent 20 when balloon 18 is inflated and the stent 20 expanded for deployment.

FIG. 5 shows an assembly generally designated 10, as shown in FIGS. 1 and 3, with balloon 18 inflated and stent 20 expanded, showing cup 22 end portion rolled proximally to release the stent 20. As noted above, the cup 22 may be elastomeric to facilitate rolling. The cup may also accordion or bunch up on itself to release the stent.

Figure 7:
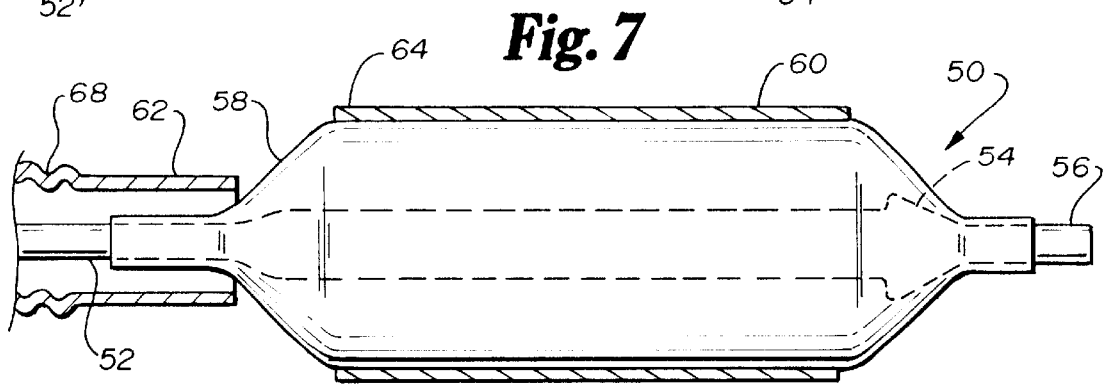
FIG. 7 is a longitudinal profile of the assembly of FIG. 6 with the balloon inflated and the stent expanded, showing the sleeve moved proximally to release the stent.

FIGS. 6 and 7 show yet another stent delivery and deployment assembly generally designated 50. The catheter 52 has a coaxial collar 54 formed integrally with catheter 52 at the catheter distal end 56. A balloon 58 is coaxially mounted on catheter 52, overlying collar 54. In FIG. 6, balloon 58 is coaxially mounted on catheter 52, overlying collar 54. In FIG. 6, balloon 58 is shown as uninflated, with an unexpanded stent 60 mounted on balloon 58 abutting collar 54, and a cylindrical cup in the form of sleeve 62 overlying the stent proximal end portion 64. FIG. 7 shows the assembly 50 of FIG. 6 with balloon 58 inflated and stent 60 released and expanded. Sleeve 62 is designed, constructed and adapted so that, as balloon 58 and stent 60 are enlarged, the sleeve portion 66 gathers or moves proximally to release stent 60. The increasing angle of the balloon 58 cone (the tapered end sections of balloon 58) during inflation push sleeve 62 axially away from stent 60. This can be done by shaping sleeve 62 with preformed accordion pleats 68. Sleeve 62 may also be formed so that the portion detaining (that is, abutting or overlying) stent 60 is of thicker or more rigid material than the portion of sleeve 62 axially distant from stent 60. Materials which may be used to provide the foregoing function are silicones, urethanes and the like as well as other elastomers, for example. A rigid sleeve carried on the catheter for sliding movement may also be used. Sleeves may be included at the proximal and distal end of the stent.

Figure 8:
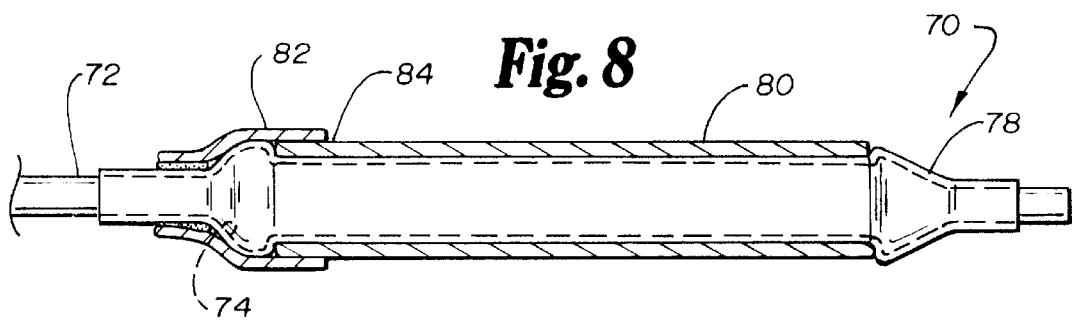
FIG. 8 is a side profile of still another stent delivery and deployment assembly of this invention with the uninflated balloon mounted on the catheter which has two collars formed integrally with the catheter, an unexpanded stent mounted on the balloon abutting the collar and a cylindrical cup overlying the stent proximal end portion and the underlying collar.

FIG. 8 shows still another stent delivery and deployment assembly generally designated 70. A catheter 72 has two collars 74 formed integrally with catheter 72 and spaced from each other on the catheter distal end portion. A balloon 78 is coaxially mounted on the catheter 72, overlying the collars 74. The balloon 78 is shown as uninflated with an unexpanded stent 80 mounted on balloon 78 abutting both of the collars 74. It can be seen that the distance between the collars 74 is to be chosen to closely accommodate stent 80 in its fully contracted position about the balloon 78 and underlying catheter 72. A cup 82 overlies the stent proximal end portion 84 and the underlying proximal collar 74. Cup 82 will deploy during balloon 78 inflation in the manner described above with reference to FIGS. 4–7.

Figure 9:
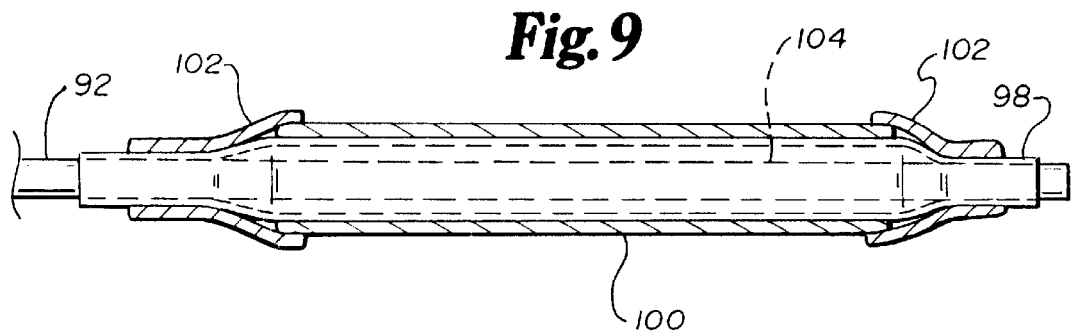
FIG. 9 is a longitudinal profile of another stent delivery and deployment assembly of this invention with the uninflated balloon mounted on the catheter, an unexpanded stent mounted on the balloon, mounting a cylinder on the catheter and a pair of cups overlying the stent ends.

FIG. 9 shows even another stent delivery and deployment assembly generally designated 90. The uninflated balloon 98 is shown coaxially mounted on a catheter 92 at the catheter distal end portion. An unexpanded stent 100 is coaxially mounted on balloon 98. A pair of cups 102 overlap the ends of the stent 100 ends. A mounting cylinder 104 is carried by the catheter shaft 92.

The Figure also illustrates cups at both ends of the stent, an arrangement which may be used in all the foregoing embodiments.

The cups or sleeves used in the various embodiments of this invention can be of elastomeric or rigid material to contain one or both ends of the stent. In preferred embodiments of this invention the cups are used in conjunction with one or more stent collars positioned under the balloon. The collar may be formed as a ring, to abut the end of the stent, to lie under the stent and the intervening balloon, or as a cylinder, to lie under essentially the entire length of the stent and the intervening balloon. The stent detainment according to the present invention offers increased stent securement, particularly on pre-mounted delivery systems. The cups and sleeves illustrated in the various embodiments of this invention can be secured to the catheter, as by adhesive or thermal bonding, or they may be sliding cups or sleeves. When the cups are freely sliding on the catheter, they should always be used directly over a collar so that there is a friction fit between the cup and the stent.

A method for delivering and deploying a stent using an assembly according to the present invention is described as follows: A catheter is provided as described above with reference to any of FIGS. 1–3, 6 and 8. At least one collar is coaxially mounted at the catheter distal end. As discussed above, the collar may be a separate element affixed to the catheter or the collar and catheter may be formed together as a single element. The collar is made of a material to which a stent and balloon may be conformed without deforming the collar. The collar may be positioned abutting an end fo the stent. The collar may be a mounting ring, may be positioned under the stent or underlying the balloon. The collar may be a cylinder essentially coextensive in length with the stent and underlying the balloon. A fluid expandable balloon is coaxially mounted over the collar on the catheter distal end. A stent is provided which is inflation expandable from a reduced to an enlarged condition. The stent, in its reduced condition, is coaxially mounted on the balloon so that at least an end portion of the stent overlies the balloon. A cup is provided which has first and second end portions. The cup is in an expanded form and also has a retracted form. The expanded cup is coaxially mounted on the catheter at the distal end portion so that the cup first end portion detains the stent end portion. The cup first end portion detains the stent end portion by overlying the stent end portion, or by closely accommodating the stent against the collar without overlying the stent end portion. The cup is then contracted about the catheter and the stent end portion to fix the stent to the catheter. The cup and collar cooperate to retain the stent on the catheter in its reduced condition. The assembly is then maneuvered by the physician through a body vessel by methods known per se to reach a preselected deployment site. The surgeon can determine when the assembly has reached the deployment site by means which are themselves known per se. For example, the assembly may be provided with radiopaque marking bands at either end of the stent, or the cups or the collars or both may be made of radiopaque material. Once the surgeon determines that the stent has been correctly positioned at the desired site, the balloon is inflated to expand the stent to its enlarged condition. Inflation of the balloon expands the stent and the stent is released from the cup or cups. As has been discussed above, the cups may deploy to release the stent in a number of ways, dependant on the construction and materials of the cup or cups. The cup may flare or enlarge radially following the increasing angle of the balloon cones. The cup may roll axially away from the stent. The portion of the cup axially distant from the stent may accordion back on itself. The cup may slide axially. The cup may accordion or buckle. If the cup is not fixed to the catheter, but is freely slidable on the catheter, the cup may slide axially away from the stent. After deployment of the stent, the balloon, according to previously known procedures, is deflated and the assembly is withdrawn proximally from the body vessel. Any incision made to allow access from the assembly is appropriately closed.

While this invention has been specifically described with reference to the representative illustrations and according to representative methods of use, there is no intention that this invention be limited other than as set out by the following claims.

What is claimed is:

1. An assembly for delivery and deployment of an inflation expandable stent, comprising:
    a catheter having proximal and distal end portions;
    an annular collar coaxially located at the catheter distal end portion;
    an expandable balloon coaxially mounted over the collar at the catheter distal end portion, the balloon being expandable from a contracted to an expanded state;
    a stent having proximal and distal end portions coaxially mounted on the balloon, the stent being expandable from a reduced to an enlarged condition, the reduced condition conforming the stent to the balloon and catheter, the stent having at least a proximal or distal end portion overlying the balloon, the collar abutting the stent as a stop;
    a cup coaxially mounted on the catheter distal end portion, the cup having a first end portion restraining the stent proximal end portion and being rigid; and
    the cup and collar cooperatively constructed and arranged to retain the stent distal and proximal end portions on the catheter in the stent reduced condition when the balloon is in the contracted state, the balloon and catheter cooperatively constructed and arranged to cause expansion of the balloon from the contracted to the expanded state and to release the stent proximal end portion from the cup end portion.

2. The assembly according to claim 1, wherein the cup is axially spaced from the collar.

3. The assembly according to claim 1, wherein the cup has a second end portion fixed to the catheter.

4. The assembly according to claim 3, wherein the second end portion is fixed with adhesive.

5. The assembly according to claim 1, wherein the cup first end portion overlies the stent end portion.

6. The assembly according to claim 1, wherein the collar is formed as a single member with the catheter.

7. The assembly according to claim 1, wherein the stent proximal or distal end portion is a distal end portion and wherein the cup and collar cooperate to retain the stent at the stent distal end portion.

8. The assembly according to claim 1, wherein the collar is axially positioned exterior to the stent at a stent distal end portion opposite the stent proximal end portion retained by the cup.

9. The assembly according to claim 8 wherein the collar is formed as a single member with the catheter.

10. The assembly according to claim 1, wherein the collar is a mounting ring axially positioned between stent end portions.

11. The assembly according to claim 10, wherein the mounting ring is formed as a single member with the catheter.

12. The assembly according to claim 10, wherein at least a portion of the mounting ring is contained by the cup.

13. The assembly according to claim 1, wherein the collar is a cylinder under the stent.

14. The assembly according to claim 13, wherein at least a portion of the cylinder is contained by the cup.

15. The assembly according to claim 13, wherein the cylinder is formed as a single member with the catheter.

16. The assembly according to claim 1, wherein a second collar is a mounting ring axially positioned between stent end portions.

17. The assembly according to claim 1, wherein a second collar is axially positioned immediately exterior to the stent at a stent end portion opposite the stent end portion retained by the cup.

18. The assembly according to claim 1, wherein the cup and the collar are each cylindrical.

19. The assembly according to claim 1, wherein the cup has a second end portion with axially running regions of weakness.

20. The assembly according to claim 1, and further including a second cup coaxially mounted on the catheter at the catheter distal end, the second cup having a first end portion overlying a stent second end portion;
    the cups and the collar cooperatively constructed and arranged to retain the respective stent end portions on the catheter in the stent reduced condition when the balloon is in the contracted state, the balloon and catheter cooperatively constructed and arranged to cause expansion of the balloon from the contracted to the expanded state to cause release of the stent end portions from the cup end portions.

21. The assembly according to claim 20, wherein the collar is formed as a single member with the catheter.

22. The assembly according to claim 20, wherein the collar is axially positioned immediately exterior to the stent at a stent end portion opposite the stent end portion retained by the cup.

23. The assembly according to claim 22, wherein the collar is shaped as a single member with the catheter.

24. The assembly according to claim 20, wherein the collar is a mounting ring axially positioned between stent end portions.

25. The assembly according to claim 24, wherein the mounting ring is shaped as a single member with the catheter.

26. The assembly according to claim 24, wherein at least a portion of the mounting ring is contained by at least one of the cups.

27. The assembly according to claim 20, wherein the collar is a cylinder coextensive with the length of the stent.

28. The assembly according to claim 27, wherein the cylinder is formed as a single member with the catheter.

29. The assembly according to claim 27, wherein at least a portion of the cylinder is contained by at least one of the cups.

30. The assembly according to claim 29, wherein each cup contains at least a portion of the cylinder.

31. The assembly according to claim 20, wherein a second collar is a mounting ring axially positioned between stent end portions.

32. The assembly according to claim 20, wherein a second collar is axially positioned immediately exterior to the stent at a stent end portion opposite the stent end portion retained by at least one of the cups.

33. The assembly according to claim 20, and further comprising fixing means for holding the collar at a specific location on the catheter.

34. The assembly according to claim 33, wherein the fixing means is adhesive.

35. An assembly for delivery and deployment of an inflation expandable stent, comprising:

a catheter having proximal and distal ends;

a mounting body carried by the catheter at the distal end portion;

an expandable balloon coaxially mounted over the catheter distal end and the mounting body, the balloon being expandable from a contracted to an expanded state;

a stent coaxially mounted on the balloon, the stent being expandable from a reduced to an enlarged condition, the reduced condition conforming the stent to the contracted balloon and catheter, the stent having an end portion overlying the balloon;

first and second cups coaxially mounted on the catheter distal end, each cup having a first end portion overlying a stent end portion, respectively, wherein at least one of the cups is rigid; and the cups constructed and arranged to retain the stent therebetween on the catheter in the stent reduced condition when the balloon is in the contracted state, the balloon and catheter cooperatively constructed and arranged to cause expansion of the balloon from the contracted to the expanded state to cause expansion of the stent, including the stent end portions, from the reduced to the enlarged condition, and thereby release the stent from abutting the cup end portions.

* * * * *

UNITED STATES PATENT AND TRADEMARK OFFICE
CERTIFICATE OF CORRECTION

PATENT NO. : 6,395,008 B1 Page 1 of 1
APPLICATION NO. : 08/701979
DATED : May 28, 2002
INVENTOR(S) : Ellis et al.

It is certified that error appears in the above-identified patent and that said Letters Patent is hereby corrected as shown below:

On the title page,
[*] delete "0" and insert --418--.

Signed and Sealed this

Fifth Day of December, 2006

JON W. DUDAS
*Director of the United States Patent and Trademark Office*